United States Patent
Huang et al.

(10) Patent No.: US 8,293,474 B2
(45) Date of Patent: Oct. 23, 2012

(54) OLIGONUCLEOTIDES AND USE THEREOF FOR DETERMINING DELETION IN HBV PRE-S REGION

(75) Inventors: Wenya Huang, Tainan (TW); Ih-Jen Su, Taipei (TW); Fang-Ching Shen, Tainan (TW)

(73) Assignee: National Health Research Institutes, Miaoli County (TW)

( * ) Notice: Subject to any disclaimer, the term of this patent is extended or adjusted under 35 U.S.C. 154(b) by 459 days.

(21) Appl. No.: 12/481,091

(22) Filed: Jun. 9, 2009

(65) Prior Publication Data

US 2010/0003668 A1 Jan. 7, 2010

Related U.S. Application Data

(60) Provisional application No. 61/077,522, filed on Jul. 2, 2008.

(51) Int. Cl.
*C12Q 1/68* (2006.01)
*C07H 21/04* (2006.01)

(52) U.S. Cl. ............ 435/6.12; 536/22.1; 536/23.1

(58) Field of Classification Search ............ None
See application file for complete search history.

(56) References Cited

OTHER PUBLICATIONS

Kleter, B. et al. Development and clinical evaluation of a highly sensitive PCR-reverse hybridization line probe assay for detection and identification of anogenital human papillomavirus. J. Clin. Microbiol., vol. 37, No. 8, p. 2508-2517, 1999.*

Tran, N. et al. European multicenter evaluation of high-density DNA probe arrays for detection of Hepatits B virus resistance mutations and identification of genotypes. J. Clin. Microbiol., vol. 44, No. 8, p. 2792-2800, 2006.*

Leaw et al., "Identification of Medically Important Candida and Non-Candida Yeast Species by an Oligonucleotide Array," *Journal of Clinical Microbiology*, vol. 45, No. 7, pp. 2220-2229 (2007).

Tung et al., "Identification of Species of *Abiotrophia, Enterococcus, Granulicatella* and *Streptococcus* by Sequence Analysis of the Ribosomal 16S-23S Intergenic Spacer Region," *Journal of Medical Microbiology*, vol. 56, pp. 504-513 (2007).

Chen et al., "Pre-S Deletion and Complex Mutations of Hepatitis B Virus Related to Advanced Liver Disease in HBeAg-Negative Patients," *Gastroenterology*, vol. 133, No. 5, pp. 1466-1474 (2007).

Ito et al., "Comparison of Complete Sequences of Hepatitis B Virus Genotype C Between Inactive Carriers and Hepatocellular Carcinoma Patients Before and After Seroconversion," *Journal of Gastroenterology*, vol. 42, pp. 837-844 (2007).

Fan et al., "Prevalence and Significance of Hepatitis B Virus (HBV) Pre-S Mutants in Serum and Liver at Different Replicative Stages of Chronic HBV Infection," *Hepatology*, vol. 33, No. 1, pp. 277-286 (2001).

* cited by examiner

*Primary Examiner* — Prabha Chunduru
(74) *Attorney, Agent, or Firm* — Occhiuti Rohlicek & Tsao LLP

(57) ABSTRACT

This invention provides combinations of novel oligonucleotides and their use in detecting a deletion(s) in the Pre-S region of HBV. Such a deletion(s) is associated with an increased risk of developing cirrhosis or hepatocellular carcinoma.

8 Claims, 6 Drawing Sheets

B.

US 8,293,474 B2

OLIGONUCLEOTIDES AND USE THEREOF FOR DETERMINING DELETION IN HBV PRE-S REGION

RELATED APPLICATION

This application claims priority to U.S. Provisional Application No. 61/077,522, filed on Jul. 2, 2008, the content of which is hereby incorporated by reference in its entirety.

BACKGROUND OF THE INVENTION

Hepatitis B virus (HBV) is a small, enveloped DNA virus that causes both acute and chronic liver diseases. Chronic HBV infection, a serious health problem in many Asian countries, often results in cirrhosis and hepatocellular carcinoma (HCC).

Deletion mutations in the Pre-S region of the HBV genome are found to be associated with an increased risk of cirrhosis and HCC. See Chen et al., Gastroenterology 133:1466-1474 (2007) and Ito et al., J. Gastroenterol. 42:837-844 (2007). It has been suggested that such deletions help HBV escape from host immune surveillance and enhance its transforming capacity. See Wang et al., Hepatology, 41:761-770 (2005).

Thus, there is a need to develop a rapid and accurate method for detecting deletions in the HBV Pre-S region, thereby assessing a HBV carrier's risk of developing cirrhosis/HCC.

SUMMARY OF THE INVENTION

The present invention is based on the discovery of a number of novel oligonucleotides for detecting deletion mutations in the Pre-S region of the HBV genome.

Accordingly, one aspect of this invention features an isolated oligonucleotide having a nucleotide sequence selected from SEQ ID NOs:1-44. The oligonucleotide can have a length of 20-50 nt (i.e., any number between 20 and 50). In one example, the oligonucleotide includes a poly(T) tail of 5-17 nucleotides (8 nt, 10 nt, or 15 nt). The term "isolated oligonucleotide" used herein refers to an oligonucleotide substantially free from naturally associated molecules, i.e., the naturally associated molecules constituting at most 20% by dry weight of a preparation containing the oligonucleotide. Purity can be measured by any appropriate method, e.g., column chromatography, polyacrylamide gel electrophoresis, and HPLC.

Another aspect of the invention relates to an oligonucleotide combination, i.e., combination (A), combination (B), or combination (C).

Oligonucleotide combination (A) contains at least 29 of the above-described oligonucleotides. Each of the 29 oligonucleotides includes a nucleotide sequence selected from SEQ ID NOs:2-30, any two of them including two different nucleotide sequences also selected from SEQ ID NOs:2-30. Preferably, this combination further contains an oligonucleotide that includes the nucleotide sequence of SEQ ID NO:1.

Oligonucleotide combination (B) contains at least 14 of the above-described oligonucleotides. Each of the 14 oligonucleotides includes a nucleotide sequence selected from SEQ ID NOs:31-44, any two of them including two different nucleotide sequences also selected from SEQ ID NOs:31-44. This combination can contain an additional oligonucleotide that includes the nucleotide sequence of SEQ ID NO:1.

Oligonucleotide combinations (A) and (B) can be merged to form oligonucleotide combination (C).

The oligonucleotides contained in combinations (A), (B), or (C) can be attached to a suitable support member to form a DNA chip.

Also within the scope of this invention is a method of using oligonucleotide combination (A), (B), or (C) for detecting a deletion(s) in the HBV Pre-S region, which includes subregions Pre-S1 and Pre-S2. Results thus obtained can be used to assess a HBV carrier's risk of developing cirrhosis or HCC. Namely, a patient who carries HBV with a deletion(s) in either the Pre-S1 or Pre-S2 region has an increased risk of developing cirrhosis or HCC relative to a HBV positive patient who carries wild-type HBV.

In one example, a test HBV DNA, obtained from a HBV-containing sample (e.g., cultured cells infected with HBV or a biosample of a HBV carrier), is hybridized with oligonucleotide combination (A) and the results thus obtained are compared with the results obtained from hybridizing the same oligonucleotide combination with wild-type HBV DNA to determine whether the test HBV DNA contains a deletion(s) in its Pre-S1 region.

In another example, a test HBV DNA, as described above, is hybridized with oligonucleotide combination (B) and the results thus obtained are compared with the results obtained from hybridizing the same oligonucleotide combination with wild-type HBV DNA to determine whether the test HBV DNA contains a deletion(s) in its Pre-S2 region.

In yet another example, a test HBV DNA is hybridized with oligonucleotide combination (C) and the results thus obtained are compared with the results obtained from hybridizing the same oligonucleotide combination with wild-type HBV DNA to determine whether the test HBV DNA contains a deletion(s) in its Pre-S region, including both Pre-S1 and Pre-S2 regions.

Combinations (A), (B), and (C) can also be used in the manufacture of kits for detecting a deletion(s) in the Pre-S region of HBV and for assessing a HBV-carrier's risk of developing cirrhosis and HCC.

The details of one or more embodiments of the invention are set forth in the description below. Other features or advantages of the present invention will be apparent from the following drawings and detailed description of an example, and also from the appended claims.

BRIEF DESCRIPTION OF THE DRAWINGS

The drawings are first described.

Figure 1:
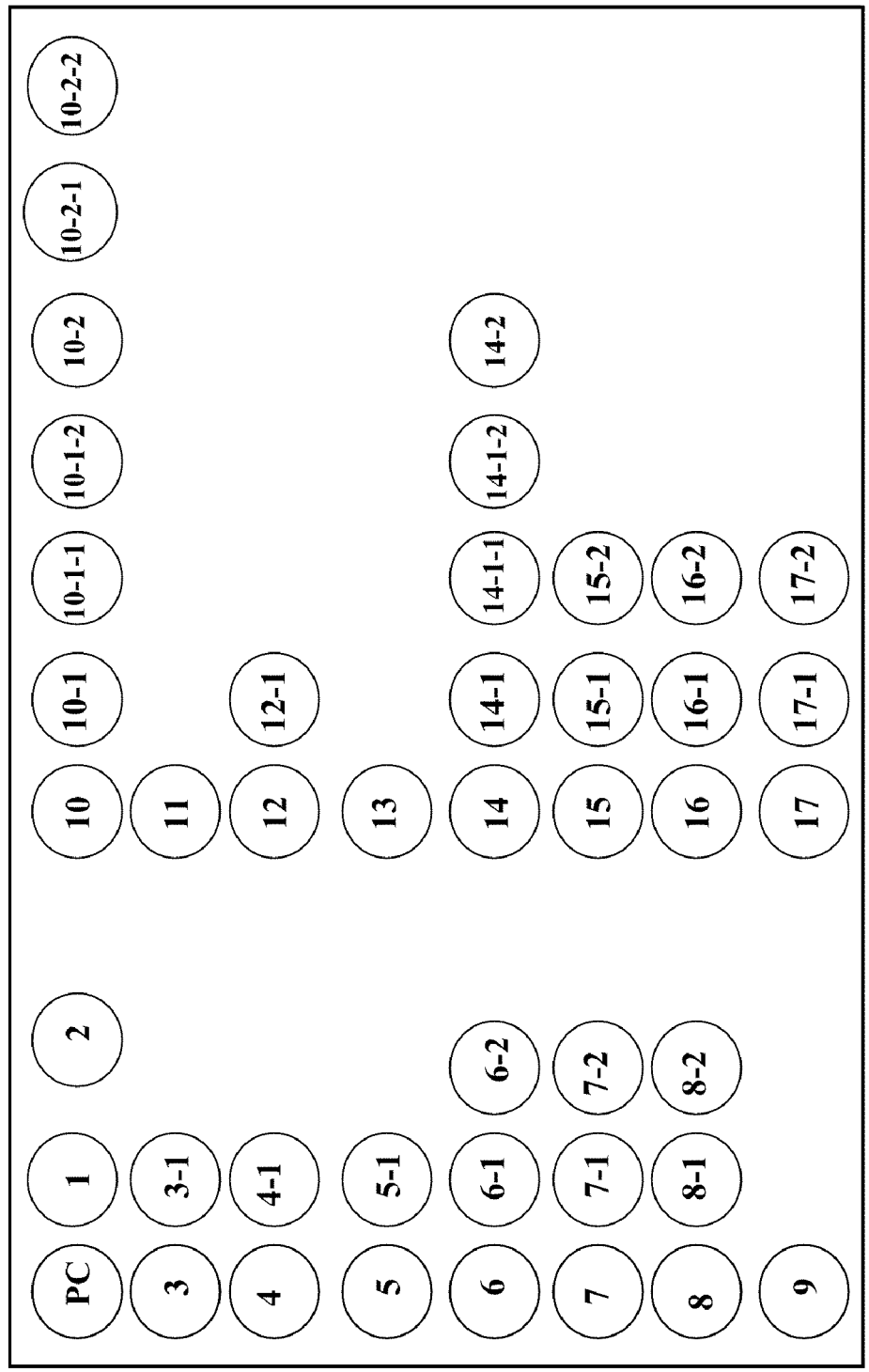
FIG. 1 is a map of a DNA chip, indicating positions of the oligonucleotides immobilized on it. PC: positive control oligonucleotide (SEQ ID NO:1; see Table 3 below). The nucleotide sequences of the other oligonucleotides are listed in Tables 1 and 2 below.

microarray results obtained from Patient 1. B: microarray results obtained from Patient 2.

DETAILED DESCRIPTION OF THE INVENTION

Disclosed herein are a number of oligonucleotide combinations for detecting a deletion(s) in the Pre-S region of HBV DNA.

The HBV Pre-S region, located at nt 2854 to 154 in the HBV genome, includes two subregions, Pre-S1 (nt 2854 to 3210) and Pre-S2 (nt 3211 to 154). See Animal Virus Genetics, pg 57-70; Academic Press, New York (1980). The length of the Pre-S region in various genotypes of wild-type HBV remains the same, even though polymorphisms have been identified at many nucleotide positions in this region. An exemplary nucleotide sequence of the wild-type HBV Pre-S region is shown below:

```
Nucleotide Sequence of Wild-Type HBV DNA Pre-S Region
                                        (SEQ ID NO: 49)
  atgggaggtt ggtcatcaaa acctcgcaaa ggcatgggga cgaatctttc      50
          R1              R2 tgttcccaat cctctgggat tctttcccga tcatcagttg gaccctgcat     100
          R3                         R4 tcggagccaa ctcaaacaat ccagattggg acttcaaccc gtcaaggac      150
            R5                                R6 gactggccag cagccaacca agtaggagtg ggagcattcg ggccaaggct     200
                              R7 caccccctcca cacggcggta ttttgggggtg gagccctcag gctcagggca   250
       R8                                 R9 tattgaccac agtgtcaaca attcctcctc ctgcctccac caatcggcag     300
                R10                                R11 tcaggaaggc agcctactcc catctctcca cctctaagag acagtcatcc     350
                             R12 tcaggccatg cagtggaatt ccactgcctt ccaccaaact ctgcaggatc     400
       R13                                R14 ccagagtcag gggtctgtat cttcctgctg gtggctccag ttcaggaaca     450
                R15                                R16 gtaaaccctg ctccgaatat tgcctctcac atctcgtcaa tctccgcgag     500
                           R17 gactggggac cctgtgacga acatggagaa catcacatca ggattcctag     550
gacccctgct cgtgttacag gcggggtttt tcttgttgac aagaatcctc     600
acaataccgc agagtctaga ctcgtggtgg acttctctca attttctagg     650
gggatctccc gtgtgtcttg gccaaaattc gcagtcccca acctccaatc     700
actcaccaac ctcctgtcct ccaatttgtc ctggttatcg ctggatgtgt     750
ctgcggcgtt ttatcatatt cctcttcatc ctgctgctat gcctcatctt     800
cttattggtt cttctggatt atcaaggtat gttgcccgtt tgtcctctaa     850
ttccaggatc aacaacaacc agtacgggac catgcaaaac ctgcacgact     900
cctgctcaag gcaactctat gtttccctca tgttgctgta caaaacctac     950
ggatggaaat tgcacctgta ttcccatccc atcgtcctgg gctttcgcaa    1000
aatacctatg ggagtgggcc tcagtccgtt tctcttggct cagtttacta    1050
gtgccatttg ttcagtggtt cgtagggctt tcccccactg tttggctttc    1100
agctatatgg atgatgtggt attggggggcc aagtctgtac agcatcgtga    1150
gtccctttat accgctgtta ccaattttct tttgtctctg ggtatacatt    1200 taa
```

Oligonucleotide combination (A) described herein contains at least 29 oligonucleotides respectively including the nucleotide sequences of SEQ ID NOs:2-30. In one example, combination (A) contains the oligonucleotides shown in Table 1 below, and preferably, an additional oligonucleotide having the nucleotide sequence of SEQ ID NO:1 (e.g., WH-PC listed in Table 3 below).

TABLE 1

Oligonucleotides Contained in An Exemplary Oligonucleotide Combination (A)

| Oligos | Position in HBV genome (Target Region) | Nucleotide Sequence (5' → 3") | SEQ ID NO |
|---|---|---|---|
| WH-1 | 2854-2873 (R1) | TTTGATGACCAACCTCCCAT | SEQ ID NO: 2 |
| WH-2 | 2874-2893 (R2) | TCCCCATGCCTTTGCGAGGT | SEQ ID NO: 3 |
| WH-3 | 2894-2923 (R3) | ATCCCAGAGGATTGGGAACAGAAAGATTCG | SEQ ID NO: 4 |
| WH-3-1 | 2894-2923 (R3) | ATCCCAGGGGATTGGGGACAGAAAGATTTG | SEQ ID NO: 5 |
| WH-4 | 2924-2953 (R4) | ATGCAGGGTCCAACTGATGATCGGGAAAGA | SEQ ID NO: 6 |
| WH-4-1 | 2924-2953 (R4) | ATGCAGGGTCCAACTGRTGATCGGGRAAGA (R: A/G) | SEQ ID NO: 7 |
| WH-5 | 2954-2983 (R5) | CCCAATCTGGATTGTTTGAGTTGGCTCCGA | SEQ ID NO: 8 |
| WH-5-1 | 2954-2983 (R5) | CCCAATCTGGATTTTCTGAGTTGGCTTTGA | SEQ ID NO: 9 |
| WH-6 | 2984-3013 (R6) | CTGGCCAGTCGTCCTTGACGGGGTTGAAGT | SEQ ID NO: 10 |
| WH-6-1 | 2984-3013 (R6) | CTGGCCADTGATCCTTGTTGGGGTTGAAGT (D: G/A/T) | SEQ ID NO: 11 |
| WH-6-2 | 2984-3013 (R6) | CCGGCCAGTTGTCCTTGTGCGGGTTGAGGT | SEQ ID NO: 12 |
| WH-7 | 3014-3043 (R7) | CGAATGCTCCCACTCCTACTTGGTTGGCTG | SEQ ID NO: 13 |
| WH-7-1 | 3014-3043 (R7) | CGAATGCTCCCACTCCCACCTTGTTGGCGG | SEQ ID NO: 14 |
| WH-7-2 | 3014-3043 (R7) | CGAATGCTCCCRCTCCTACCTGRTTKGCCG (R: A/G; K: G/T) | SEQ ID NO: 15 |
| WH-8 | 3044-3073 (R8) | TACCGCCGTGTGGAGGGGTGAGCCTTGGCC | SEQ ID NO: 16 |
| WH-8-1 | 3044-3073 (R8) | CACCGCCGTGTGGWGGGRTGAACCCTGGCC (W: A/T; R: A/G) | SEQ ID NO: 17 |
| WH-8-2 | 3044-3073 (R8) | GTCCCCCATGGGGAGGGRTGAACCCTGGCC (R: A/G) | SEQ ID NO: 18 |
| WH-9 | 3074-3103 (R9) | TGCCCTGAGCCTGAGGGCTCCACCCCAAAA | SEQ ID NO: 19 |
| WH-10 | 3104-3133 (R10) | GAGGAGGAATTGTTGACACTGTGGTCAATA | SEQ ID NO: 20 |
| WH-10-1 | 3104-3133 (R10) | GAGGAGGAGCTGCTGGCACAGTTGTGAGTA | SEQ ID NO: 21 |
| WH-10-1-1 | 3088-3117 (R10) | CACAGTTGTGAGTATGCCCTGAGCCTGAGG | SEQ ID NO: 22 |
| WH-10-1-2 | 3118-3147 (R10) | ATTGGTGGAGGCAGGAGGAGGAGCTGCTGG | SEQ ID NO: 23 |

TABLE 1-continued

Oligonucleotides Contained in An Exemplary Oligonucleotide Combination (A)

| Oligos | Position in HBV genome (Target Region) | Nucleotide Sequence (5' → 3") | SEQ ID NO |
|---|---|---|---|
| WH-10-2 | 3104-3133 (R10) | GAGGAGGNGCTRCTGGCACTGTTGTCARTA (N: A/T/C/G; R: A/G) | SEQ ID NO: 24 |
| WH-10-2-1 | 3088-3117 (R10) | CACTGTTGTCARTATGCCCTGAGCCTGAGG (R: A/G) | SEQ ID NO: 25 |
| WH-10-2-2 | 3118-3147 (R10) | ATTGGTGGAGGCAGGAGGAGGNGCTRCTGG (N: A/T/C/G; R: A/G) | SEQ ID NO: 26 |
| WH-11 | 3134-3163 (R11) | GCCTTCCTGACTGCCGATTGGTGGAGGCAG | SEQ ID NO: 27 |
| WH-12 | 3164-3193 (R12) | CTCTTAGAGGTGGAGAGATGGGAGTAGGCT | SEQ ID NO: 28 |
| WH-12-1 | 3164-3193 (R12) | CTCTTAGAGGTGGAGATAAGGGAGTAGGCT | SEQ ID NO: 29 |
| WH-13 | 3194-0002 (R13) | AATTCCACTGCATGGCCTGAGGATGACTGT | SEQ ID NO: 30 |

Oligonucleotide combination (B) contains at least 14 oligonucleotides respectively including the nucleotide sequences of SEQ ID NOs:31-44. In one example, this combination contains the oligonucleotides shown in Table 2 below, and preferably, an additional oligonucleotide having the nucleotide sequence of SEQ ID NO:1 (e.g., WH-PC listed in Table 3 below).

TABLE 2

Oligonucleotides Contained in An Exemplary Oligonucleotide Combination (B)

| Oligos | Position in HBV genome | Nucleotide Sequence (5' → 3") | SEQ ID NO |
|---|---|---|---|
| WH-14 | 0003-0032 (R14) | GATCCTGCAGAGTTTGGTGGAAGGCAGTGG | SEQ ID NO: 31 |
| WH-14-1 | 0005-0031 (R14) | ATCTTGAAGAGTTTGGTGGAAAGTGGT | SEQ ID NO: 32 |
| WH-14-1-1 | 0003-0032 (R14) | GATCTTGAAGAGTTTGGTGGAAGGTGGTGG | SEQ ID NO: 33 |
| WH-14-1-2 | 0005-0031 (R14) | ATCTTGAAGAGTTTGGTGGAAGGTGGT | SEQ ID NO: 34 |
| WH-14-2 | 0005-0031 (R14) | GATCTTGCAGAGCTTGGTGGAATGTTGTGG | SEQ ID NO: 35 |
| WH-15 | 0033-0062 (R15) | CAGCAGGAAGATACAGACCCCTGACTCTGG | SEQ ID NO: 36 |
| WH-15-1 | 0035-0061 (R15) | AGCAGGAARGTACAGGGCCCTGACTCT (R: A/G) | SEQ ID NO: 37 |
| WH-15-2 | 0033-0062 (R15) | CAGCAGGAAARTAYAGGCCCCTCACTCTGG (R: A/G; Y: T/C) | SEQ ID NO: 38 |
| WH-16 | 0063-0092 (R16) | CAGGGTTTACTGTTCCTGAACTGGAGCCAC | SEQ ID NO: 39 |
| WH-16-1 | 0063-0092 (R16) | CAGGGCTCACTGTTCCTGAACTGGAGCCAC | SEQ ID NO: 40 |
| WH-16-2 | 0063-0092 (R16) | CAGGGTTTACTGTTCCKGAACTGGAGCCAC (K: G/T) | SEQ ID NO: 41 |
| WH-17 | 0093-0122 (R17) | TTGACGAGATGTGAGAGGCAATATTCGGAG | SEQ ID NO: 42 |

TABLE 2-continued

Oligonucleotides Contained in An Exemplary Oligonucleotide Combination (B)

| Oligos | Position in HBV genome | Nucleotide Sequence (5' → 3") | SEQ ID NO |
|---|---|---|---|
| WH-17-1 | 0093-0122 (R17) | TTGACGATATGGYMGAGACAGTATTCTGAG (Y: T/C; M: C/A) | SEQ ID NO: 43 |
| WH-17-2 | 0093-0122 (R17) | TTGACGATATGGGWGAGGCAGTAGTCGGAA (W: A/T) | SEQ ID NO: 44 |

Combinations (A) and (B) can be merged to form combination (C). In one example, combination (C) contains the oligonucleotides listed in both Tables 1 and 2 above, as well as WH-PC listed in Table 3 below.

Combinations (A), (B), or (C) described above can be used for detecting a deletion(s) in the Pre-S region of HBV via hybridization. More specifically, combination (A) is used for detecting a deletion(s) in the Pre-S1 region of HBV, combination (B) is used for detecting a deletion(s) in the Pre-S2 region, and combination (C) is used for detecting a deletion(s) in the whole Pre-S region. The oligonucleotides contained in these two combinations target regions R1-R17 (shown in SEQ ID NO: 49 above) in the Pre-S region as indicated in Tables 1 and 2 above. Each of the combinations include multiple oligonucleotides that target the same region (e.g., R10 or R14) where polymorphisms exist in different viral genotypes. Thus, the two combinations can be used for detecting Pre-S deletions in a HBV without first determining its particular genotype. When included in any of combinations (A), (B), and (C), WH-PC, having the nucleotide sequence of SEQ ID NO:1, serves as a positive control.

All of the oligonucleotides described above can be made by conventional methods, e.g., chemical synthesis. Preferably, oligonucleotides of combination (A), (B), or (C) are immobilized onto the surface of a suitable support member (e.g., a polymer substrate) via a linker (e.g., a poly T tail) to form a DNA chip. The poly(T) linker, including 5-17 nt, can be located at either the 5' or 3' end of an oligonucleotide. The support member can be made of various materials, e.g., glass, plastic, nylon, or silicon.

The DNA chip mentioned above can be hybridized with a test HBV DNA sample under suitable hybridization conditions, such as hybridization at 48-55° C. (e.g., 50 or 55° C.) and washing with <0.5×SSC (e.g., 0.2×SSC, 0.1×SSC, or any equivalent wash buffer) at 23-28° C. In a preferable example, the test HBV DNA is prepared via PCR amplification with the primers listed in Table 3 below from a biosample (e.g., a serum or liver sample) of a HBV positive patient. When the PCR product yields a single band on an agrose gel, it can be used directly for the just-mentioned hybridization assay. When the PCR product yields multiple bands on an agrose gel, DNAs of each band can be eluted from the gel, cloned into a vector, and then subjected to another PCR reaction to generate HBV DNA suitable for the hybridization assay.

TABLE 3

Oligonucleotides Used as Positive Control and PCR Primers

| Oligos | Position in HBV genome | Nucleotide Sequence (5' → 3") | SEQ ID NO |
|---|---|---|---|
| WH-PC | 2818-2837 | GCGGGTCACCATATTCTTGG | SEQ ID NO: 1 |
| WH-1 Rev | 0236-0255 | GAGTCTAGACTCTGCGGTAT | SEQ ID NO: 45 |
| WH-2 Rev | 0180-0199 | TAACACGAGCAGGGGTCCTA | SEQ ID NO: 46 |

The hybridization results thus obtained are then compared with results obtained from hybridizing the same DNA chip with a wild-type HBV DNA to determine whether the test HBV DNA contains a deletion(s) in its Pre-S region. For example, failure to hybridize to all of the oligonucleotides that target the same region (e.g., R8 or R14) indicates that the test HBV DNA contains a deletion(s) in that region.

Without further elaboration, it is believed that one skilled in the art can, based on the above description, utilize the present invention to its fullest extent. The following specific example is, therefore, to be constructed as merely illustrative, and not limitative of the remainder of the disclosure in any way whatsoever. All publications cited herein are incorporated by reference.

Determination of Deletions in HBV Pre-S1 and Pre-S2 Regions by Microarray Analysis a. Preparation of an Oligo Microarray Chip for Determining Deletions in the Pre-S1 and Pre-S2 Regions of HBV Each of the oligonucleotides listed in both Table 1 and Table 2 and oligonucleotide WH-PC listed in Table 3 was dissolved separately in a buffer containing glycerol, dimethyl sulfoxide, sodium EDTA, and bromophenol blue at a final concentration of 20 µM. All of these oligonucleotides were then spotted onto a positively charged nylon membrane by an Ezspot arrayer using a 400 µm diameter solid pin and exposed to a shortwave UV for 30 s to form a DNA microarray chip. FIG. 1 shows the positions of each of the oligonucleotides on the DNA chip.

b. Preparation of HBV DNA Samples for Microarray Analysis

HBV DNA samples obtained from HBV positive patients were prepared as follows. Serum samples were collected from these patients and DNAs were isolated from the samples by QIAamp MinElute Virus Spin following the instruction of the manufacturer. Briefly, 200 µl of each serum sample were mixed with 25 µl QIAGEN protease and 200 µl Buffer AL (containing 28 µg/ml of carrier RNAs). The mixture thus formed was incubated at 56° C. for 15 min in a heating block.

After being mixed with 250 µl of ethanol (96-100%), the mixture was subjected to pulse-vortex for 15 sec, and then incubation at room temperature for 5 min. The lysate thus formed was carefully loaded onto a QIAamp MinElute column, which was centrifuged at 6000×g (8000 rpm) for 1 min., and the collection tube containing the filtrate was discarded. The column was washed twice with Buffer AW2 and ethanol, centrifuged at a full speed (20000×g; 14000 rpm) for 3 min to dry completely the membrane contained in the column. 20-150 µl of Buffer AVE or RNase-free water were added to the center of the membrane in the column. After being incubated at room temperature for 1 min, the column was centrifuged at a full speed (20000×g; 14000 rpm) for 1 min to collect a solution containing DNAs.

The DNAs thus obtained were used as PCR templates for preparing DNAs including the HBV Pre-S region, using the primers of $W_H$-PC: 5'-GCGGGTCACCATATTCTTGG-3' (forward primer; SEQ ID NO:1), and WH-1-Rev: 5'-GAGTCTAGACTCTGCGGTAT-3' (SEQ ID NO:45), and WH-2 Rev.: 5'-TAACACGAGCAGGGGTCCTA-3' (SEQ ID NO:46). See Table 3 above. Both primers were labeled with digoxigenin (DIG) at their 5' ends. The PCR amplification was carried out under the following conditions: (a) initial denaturation at 95° C. for 3 min; (b) 35 cycles of denaturation at 95° C. for 1 min, annealing at 58° C. for 40 sec, and extension at 72° C. for 45 sec; and (c) final extension at 72° C. for 8 min. The PCR products were examined by agarose gel electrophoresis. If the DNA products yield a single band on the electrophoresis gel, they were analyzed via a microarray assay described below to examine for Pre-S a deletion(s). If two or more bands were produced, the PCR products were subjected to TA cloning and colony PCR as described below.

C. TA Cloning and Colony PCR

The PCR products prepared by the method described above were subjected to agarose gel electrophoresis and each DNA band on the gel was eluted from the gel. The eluted PCR products were ligated with a TA cloning vector in a ligation system containing 1 µl of 10× ligation buffer A, 1 µl of 10× ligation buffer B, 2 µl of TA vector, 5 µl of PCR product, and 1 µl of T4 DNA ligase. The ligation reaction was carried out at 22° C. for 15 min. The products thus obtained were transformed into host cells (*E. coli* DH5α) and selected on Ampicillin-selective medium for positive transformants. The colonies of the positive transformants were picked up for colony PCR, using the M13 vector primers M13 F: 5'-GTTTTC-CCAGTCACGAC-3 (SEQ ID NO:47), and M13 R: 5'-TCA-CACAGGAAACAGCTATGAC-3' (SEQ ID NO:48). The PCR products were then re-amplified with the DIG-labeled $W_H$-For and $W_H$-Rev primers described in section b above, following the PCR reaction conditions also described therein.

d. Microarray Analysis

The microarray chip described in section a above was prehybridized for 2 hours in a hybridization solution containing 5×SSC, 1% blocking reagent, 0.1% N-lauroylsarcosine, 0.02% SDS). The digoxigenin-labeled PCR products described in section b above, corresponding to the HBV Pre-S region, were heated at 95° C. for 5 min and immediately cooled in an ice bath to denature the PCR products. Ten microliters of each denatured PCR product, diluted in 0.3 ml of the hybridization solution, were mixed with the prehybridized microarray chip and the hybridization reaction was carried out at 50° C. for 90 min. After washing away the nonhybridized DNA molecules, the microarray chip was washed four times with 0.1×SSC-0.2% SDS at 25° C., followed by incubation for 1 h in a blocking buffer (a Maleic acid buffer purchased from Roche). The blocking buffer was then removed and the microarray chip was incubated with a solution containing alkaline phosphatase-conjugated anti-DIG antibodies (1:1250 dilution) for 1 hr. After being washed three times (10 min each time) with a MAB washing solution that contains 0.1 M Maleic acid, 0.15 M NaCl, (pH 7.5), the chip was incubated for 5 min with a detection buffer (0.1 M Tris-HCl, 0.1 M NaCl, pH 9.5). A solution containing nitro blue tetrazolium chloride/5-bromo-4-chloro-3-indolyl phosphate, an alkaline phosphate substrate, was incubated with the chip at 37° C. for 15 min without shaking. Afterwards, the chip was washed three times with distilled water, air-dried, and examined for positive signals (dark purple color) developed at positions where the PCR products hybridized with the oligonucleotides immobilized thereon.

Figure 2:
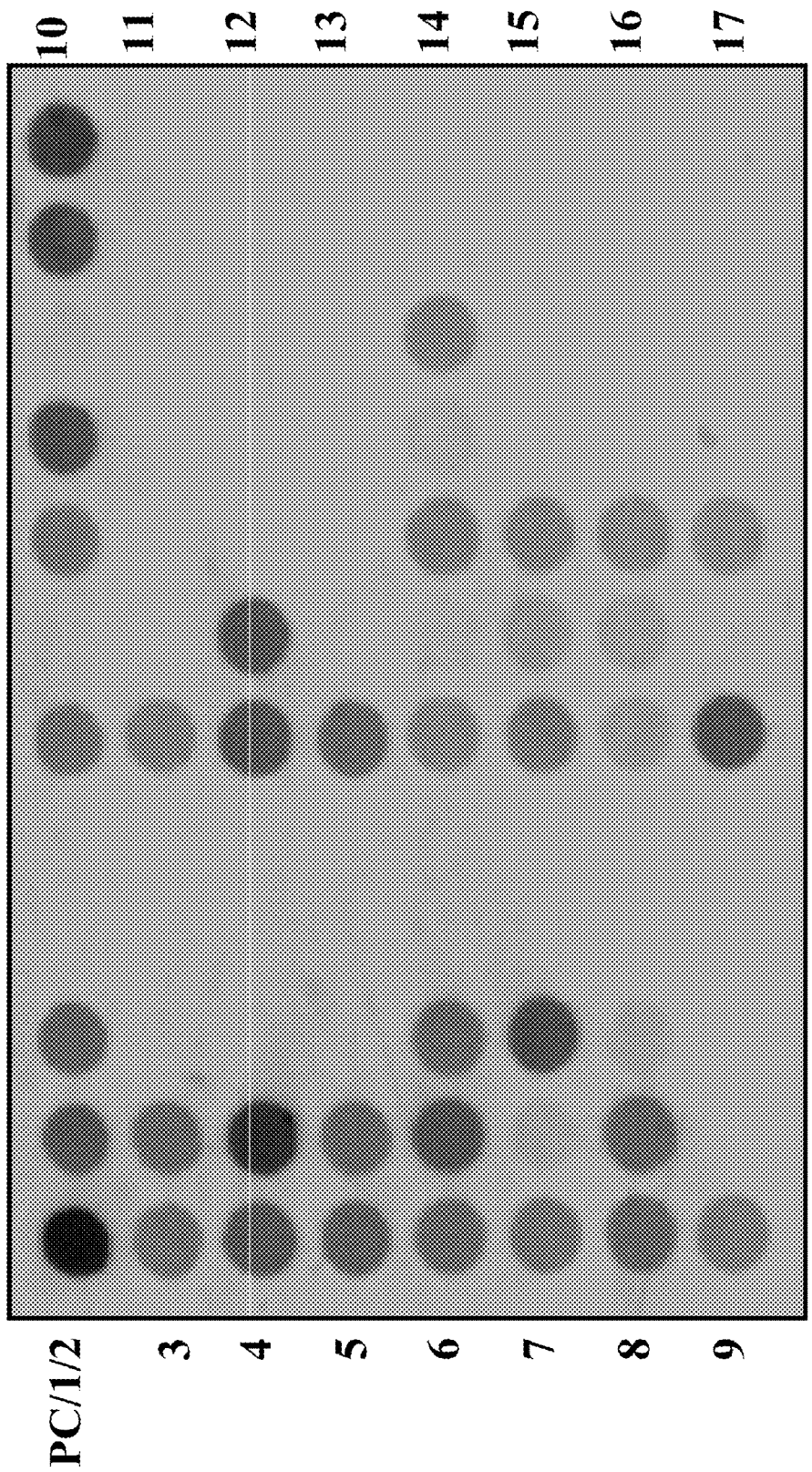
FIG. 2 is a photograph showing microarray results obtained from hybridizing wild-type HBV DNA with a DNA chip. The oligonucleotides contained in the DNA chip and their positions thereon are shown in the map of FIG. 1.
Figure 3:
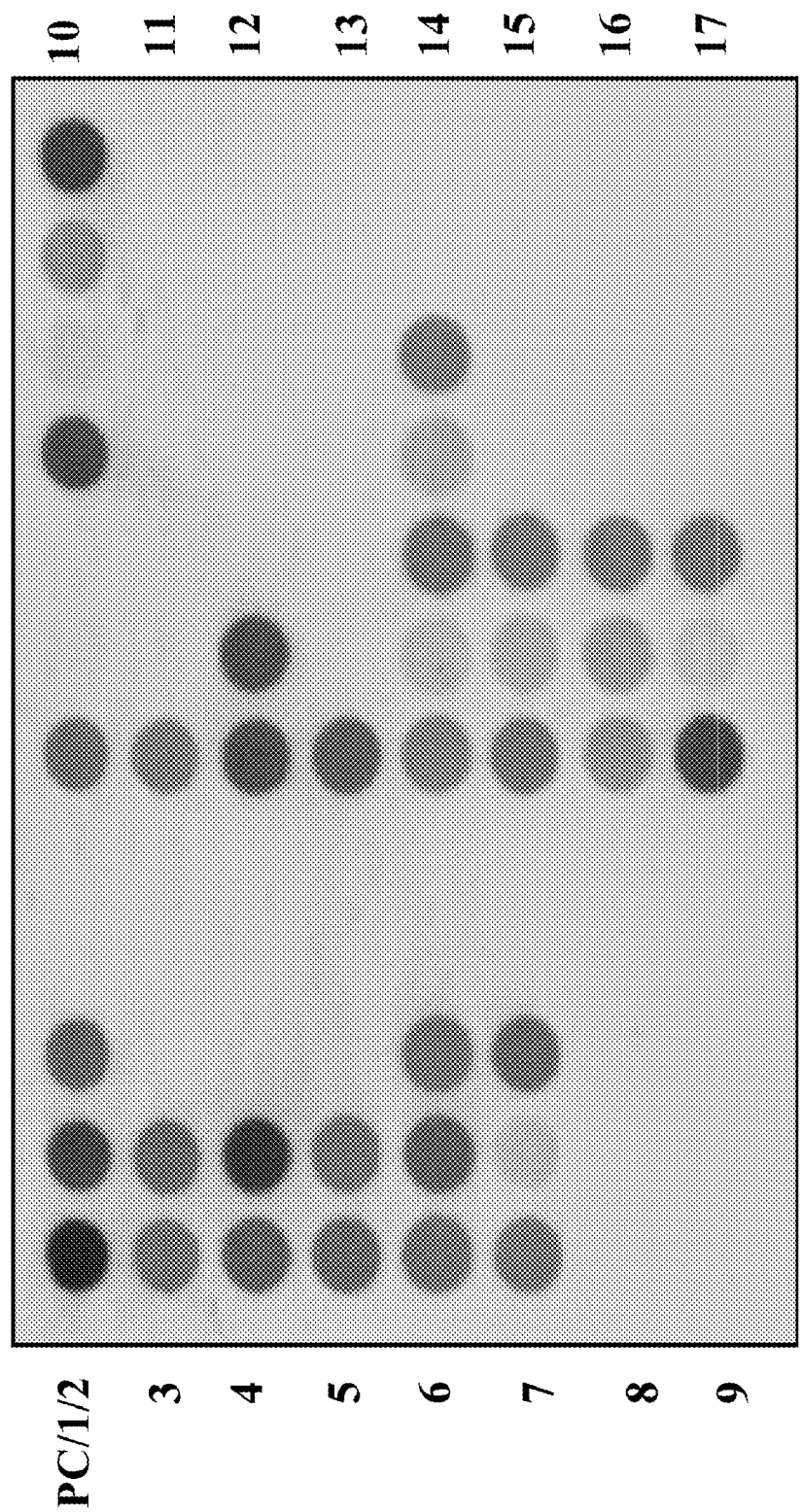
FIG. 3 is a photograph showing microarray results obtained from hybridizing HBV DNA bearing deletions in either the Pre-S1 or Pre-S2 region with the DNA chip described above. A: microarray results using HBV DNA bearing deletions in the Pre-S1 region. B: microarray results using HBV DNA bearing deletions in the Pre-S2 region.
Figure 3:
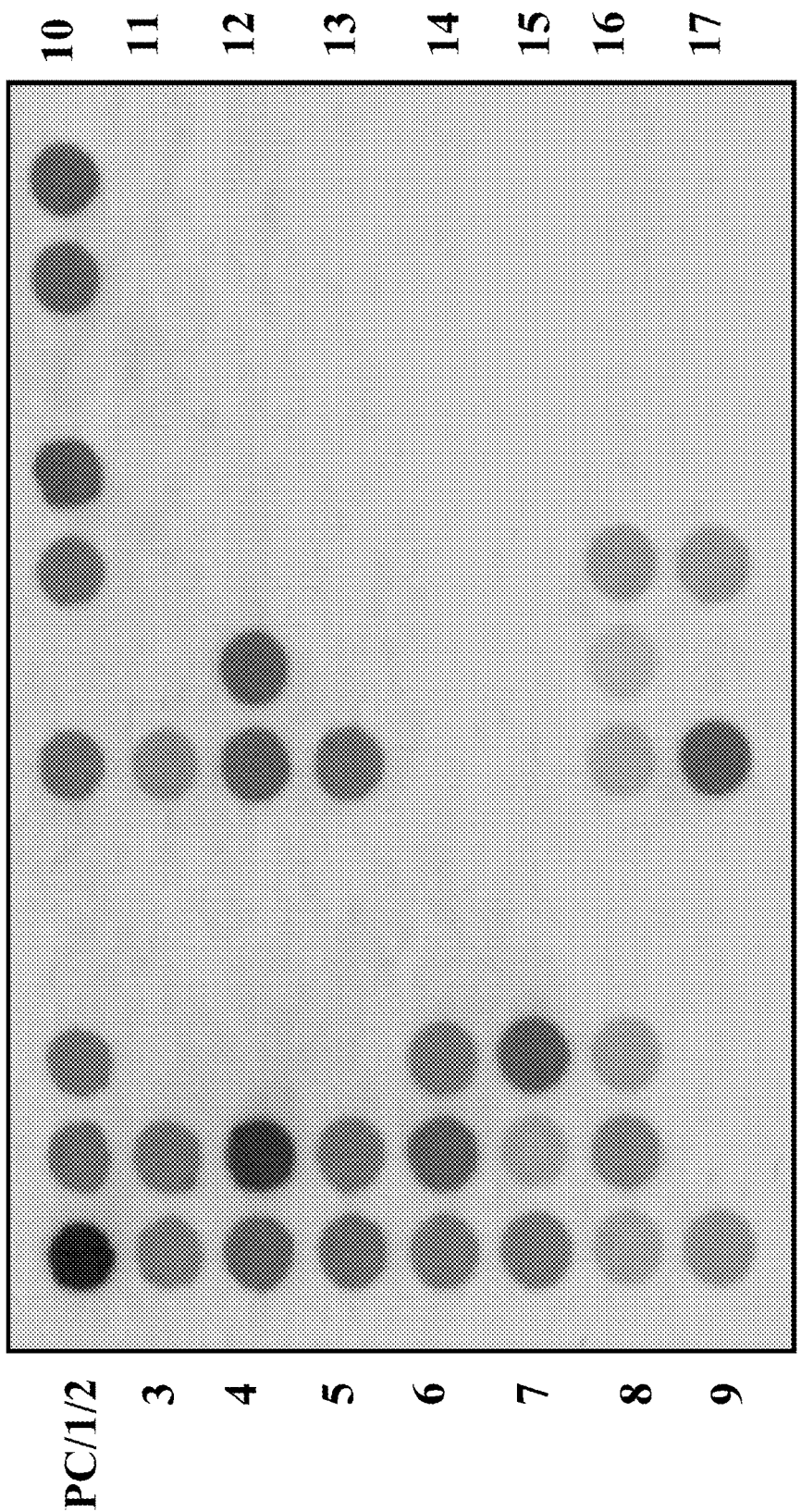

The microarray results obtained from hybridizing a wild-type HBV DNA with the DNA chip described above are shown in FIG. 2. The wild-type HBV DNA hybridizes to at least one oligonucleotide that targets each of regions R1-R17. As shown in FIG. 3, a HBV DNA having deletions in the Pre-S1 region does not hybridize to any of the oligonucleotides that target regions R8 and R9 (see panel A), indicating that there are Pre-S1 deletions located within these two regions. Also shown in FIG. 3, a HBV DNA having deletions in the Pre-S2 region does not hybridize to any of the oligonucleotides that target regions R14 and R15 (see panel B), indicating that the Pre-S2 deletions locate within these two regions.

Figure 4:
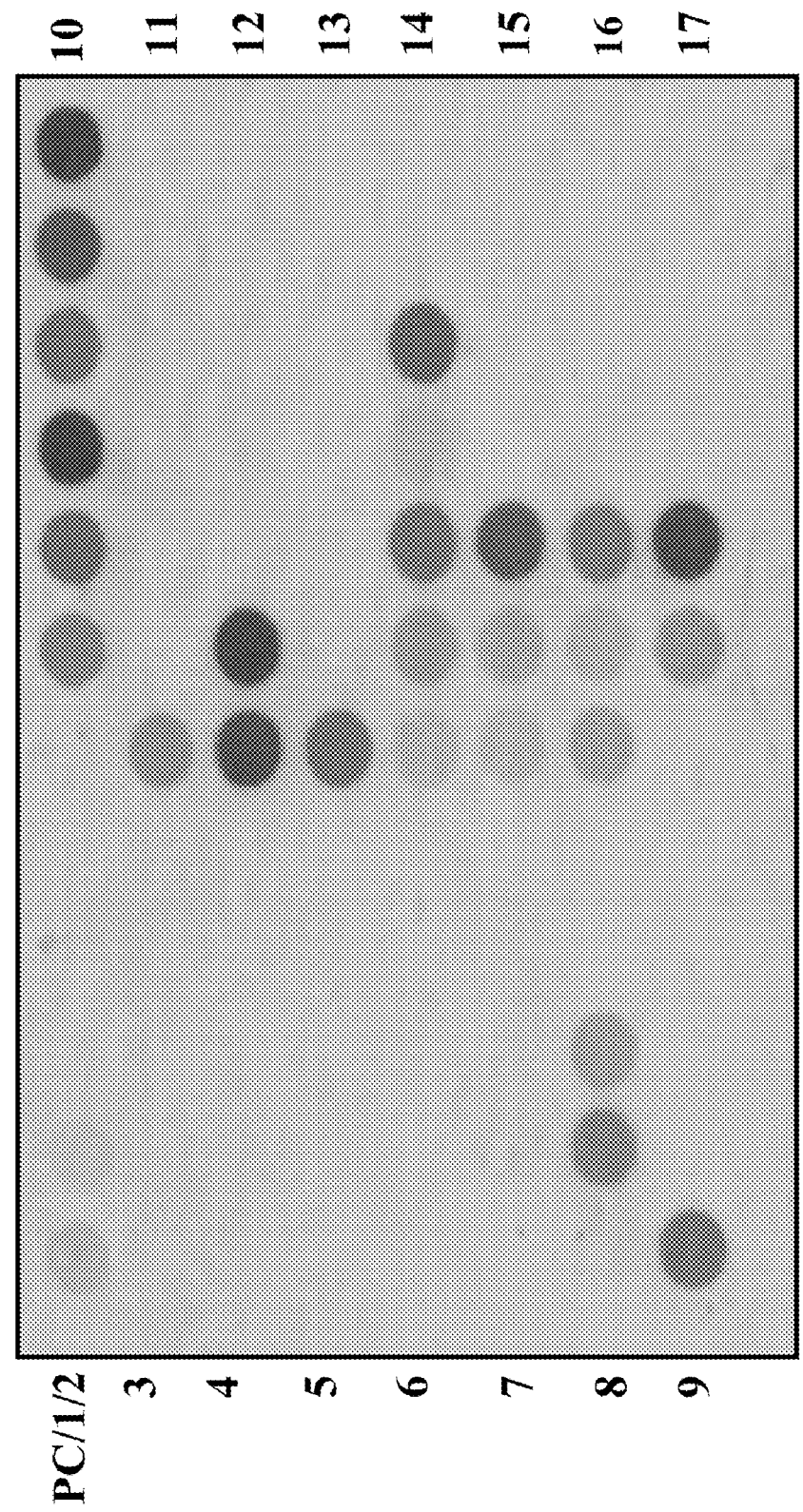
FIG. 4 is a photograph showing microarray results obtained from hybridizing DNA samples prepared from two HBV positive patients with the DNA chip described above. A.
Figure 4:
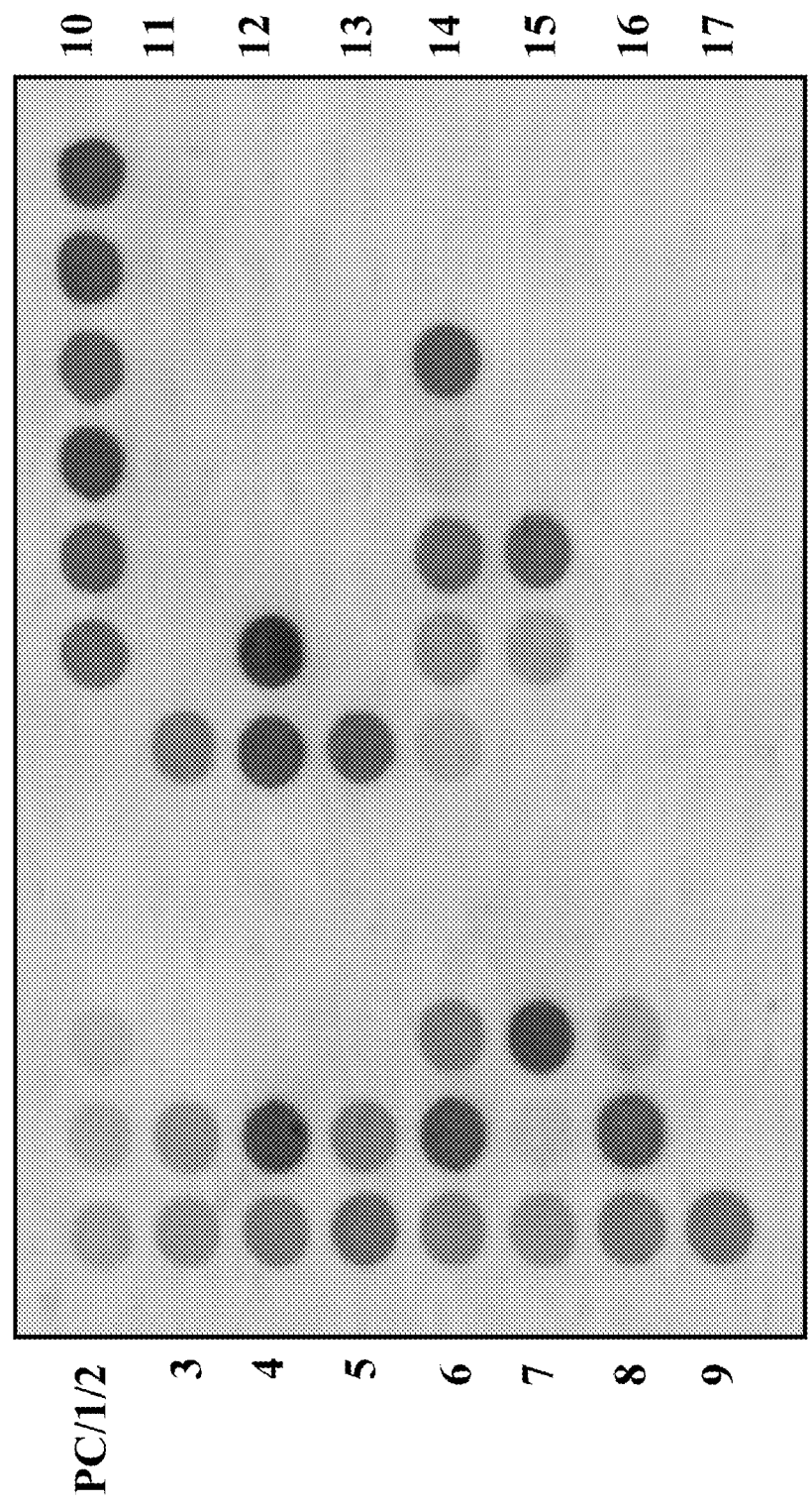

HBV DNA samples, obtained from two HBV positive patients, were subjected to the microarray analysis described above. As shown in FIG. 4, the HBV DNA obtained from Patient 1 does not hybridize to any of the oligonucleotides targeting regions R2 to R7 (see Panel A) and the HBV DNA from Patient 2 does not hybridize to any of the oligonucleotides targeting regions R16 and R17 (see Panel B). These results indicate that Patients 1 and 2 carry HBV with deletions in the Pre-S1 and Pre-S2 regions, respectively. The HBV DNAs from both Patient 1 and Patient 2 were subjected to DNA sequencing and the results thus obtained were consistent with those obtained from the microarray assay described above.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An oligonucleotide combination of 43 oligonucleotides, comprising the sequences of SEQ ID NO: 2-44, wherein each of the 43 oligonucleotides has a length of 20-50 nucleotides and specifically hybridizes to a target nucleotide sequence within wild-type HBV Pre-S region.

2. The oligonucleotide combination of claim 1, further comprising an oligonucleotide including the nucleotide sequence of SEQ ID NO:1 and having a length of 20-50 nt.

3. The oligonucleotide combination of claim 2, wherein each of the oligonucleotides has a 5-17-nt-long poly(T) tail.

4. The oligonucleotide combination of claim 3, wherein all of the oligonucleotides are attached to a support member to form a DNA chip.

5. A method of detecting a deletion in HBV Pre-S region, comprising:
    obtaining HBV DNA from a biosample,
    hybridizing the HBV DNA with the oligonucleotide combination of claim 1, and
    determining whether the HBV DNA has a deletion in its Pre-S region, wherein failure of the HBV DNA to hybridize to at least one oligonucleotide of the oligonucleotide combination that specifically hybridizes to the target nucleotide sequence indicates that the HBV DNA has a deletion in its Pre-S region located within a region containing the target nucleotide sequence.

6. The method of claim 5, wherein the HBV DNA is further hybridized with a 20-50-nt-long oligonucleotide that includes the nucleotide sequence of SEQ ID NO:1 as a positive control.

7. A method of assessing whether a patient carrying HBV has an increased risk of developing hepatocellular carcinoma (HCC) or cirrhosis, comprising:
    obtaining HBV DNA from a patient carrying HBV;
    hybridizing the HBV DNA with the oligonucleotide combination of claim 1;
    determining whether the HBV DNA has a deletion in its Pre-S region, wherein failure of the HBV DNA to hybridize to at least one oligonucleotide of the oligonucleotide combination that specifically hybridizes to the target nucleotide sequence indicates that the HBV DNA has a deletion in its Pre-S region located within a region containing the target nucleotide sequence; and
    assessing the patient's risk of developing HCC or cirrhosis, wherein the deletion in the Pre-S region indicates that the patient has an increased risk of developing HCC or cirrhosis relative to a patient carrying wild-type HBV.

8. The method of claim 7, wherein the HBV DNA is further hybridized with a 20-50-nt-long oligonucleotide that includes the nucleotide sequence of SEQ ID NO:1 as a positive control.

* * * * *

SEQUENCE LISTING

<160> NUMBER OF SEQ ID NOS: 49

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
gcgggtcacc atattcttgg                                              20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
tttgatgacc aacctcccat                                              20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
tccccatgcc tttgcgaggt                                              20

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide

<400> SEQUENCE: 4
atcccagagg attgggaaca gaaagattcg                                   30

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide

<400> SEQUENCE: 5
atcccagggg attggggaca gaaagatttg                                   30

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide

<400> SEQUENCE: 6
atgcagggtc caactgatga tcgggaaaga                                   30

<210> SEQ ID NO 7
<211> LENGTH: 30
<212> TYPE: DNA

```
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (17)..(17)
<223> OTHER INFORMATION: r is a or g
<220> FEATURE:
<221> NAME/KEY: misc_feature
<222> LOCATION: (26)..(26)
<223> OTHER INFORMATION: r is a or g

<400> SEQUENCE: 7
atgcagggtc caactgrtga tcgggraaga                                    30

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide

<400> SEQUENCE: 8
cccaatctgg attgtttgag ttggctccga                                    30

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide

<400> SEQUENCE: 9
cccaatctgg attttctgag ttggctttga                                    30

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide

<400> SEQUENCE: 10
ctggccagtc gtccttgacg gggttgaagt                                    30

<210> SEQ ID NO 11
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (8)..(8)
<223> OTHER INFORMATION: d is g, a, or t

<400> SEQUENCE: 11
ctggccadtg atccttgttg gggttgaagt                                    30

<210> SEQ ID NO 12
<211> LENGTH: 30
<212> TYPE: DNA
<213> ORGANISM: Artificial Sequence
<220> FEATURE:
<223> OTHER INFORMATION: Oligonucleotide

<400> SEQUENCE: 12
ccggccagtt gtccttgtgc gggttgaggt                                    30
```

```
<210> SEQ ID NO 13
<211> LENGTH: 30
<212> TYPE: DNA
<213> ORGANISM: Artificial Sequence
<220> FEATURE:
<223> OTHER INFORMATION: Oligonucleotide

<400> SEQUENCE: 13
cgaatgctcc cactcctact tggttggctg                                        30

<210> SEQ ID NO 14
<211> LENGTH: 30
<212> TYPE: DNA
<213> ORGANISM: Artificial Sequence
<220> FEATURE:
<223> OTHER INFORMATION: Oligonucleotide

<400> SEQUENCE: 14
cgaatgctcc cactcccacc ttgttggcgg                                        30

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (12)..(12)
<223> OTHER INFORMATION: r is a or g
<220> FEATURE:
<221> NAME/KEY: misc_feature
<222> LOCATION: (23)..(23)
<223> OTHER INFORMATION: r is a or g
<220> FEATURE:
<221> NAME/KEY: misc_feature
<222> LOCATION: (26)..(26)
<223> OTHER INFORMATION: k is g or t

<400> SEQUENCE: 15
cgaatgctcc crctcctacc tgrttkgccg                                        30

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide

<400> SEQUENCE: 16
taccgccgtg tggaggggtg agccttggcc                                        30

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (14)..(14)
<223> OTHER INFORMATION: w is a or t
<220> FEATURE:
<221> NAME/KEY: misc_feature
<222> LOCATION: (18)..(18)
<223> OTHER INFORMATION: r is a or g

<400> SEQUENCE: 17
caccgccgtg tggwgggrtg aaccctggcc                                        30
```

```
<210> SEQ ID NO 18
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: r is a or g

<400> SEQUENCE: 18
gtcccccatg gggagggrtg aaccctggcc                                        30

<210> SEQ ID NO 19
<211> LENGTH: 30
<212> TYPE: DNA
<213> ORGANISM: Artificial Sequence
<220> FEATURE:
<223> OTHER INFORMATION: Oligonucleotide

<400> SEQUENCE: 19
tgccctgagc ctgagggctc caccccaaaa                                        30

<210> SEQ ID NO 20
<211> LENGTH: 30
<212> TYPE: DNA
<213> ORGANISM: Artificial Sequence
<220> FEATURE:
<223> OTHER INFORMATION: Oligonucleotide

<400> SEQUENCE: 20
gaggaggaat tgttgacact gtggtcaata                                        30

<210> SEQ ID NO 21
<211> LENGTH: 30
<212> TYPE: DNA
<213> ORGANISM: Artificial Sequence
<220> FEATURE:
<223> OTHER INFORMATION: Oligonucleotide

<400> SEQUENCE: 21
gaggaggagc tgctggcaca gttgtgagta                                        30

<210> SEQ ID NO 22
<211> LENGTH: 30
<212> TYPE: DNA
<213> ORGANISM: Artificial Sequence
<220> FEATURE:
<223> OTHER INFORMATION: Oligonucleotide

<400> SEQUENCE: 22
cacagttgtg agtatgccct gagcctgagg                                        30

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide

<400> SEQUENCE: 23
attggtggag gcaggaggag gagctgctgg                                        30

<210> SEQ ID NO 24
<211> LENGTH: 30
<212> TYPE: DNA
```

```
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (8)..(8)
<223> OTHER INFORMATION: n is a, t, c, or g
<220> FEATURE:
<221> NAME/KEY: misc_feature
<222> LOCATION: (12)..(12)
<223> OTHER INFORMATION: r is a or g
<220> FEATURE:
<221> NAME/KEY: misc_feature
<222> LOCATION: (28)..(28)
<223> OTHER INFORMATION: r is a or g

<400> SEQUENCE: 24
gaggaggngc trctggcact gttgtcarta                                    30

<210> SEQ ID NO 25
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (12)..(12)
<223> OTHER INFORMATION: r is a or g

<400> SEQUENCE: 25
cactgttgtc artatgccct gagcctgagg                                    30

<210> SEQ ID NO 26
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (22)..(22)
<223> OTHER INFORMATION: n is a, t, c, or g
<220> FEATURE:
<221> NAME/KEY: misc_feature
<222> LOCATION: (26)..(26)
<223> OTHER INFORMATION: r is a or g

<400> SEQUENCE: 26
attggtggag gcaggaggag gngctrctgg                                    30

<210> SEQ ID NO 27
<211> LENGTH: 30
<212> TYPE: DNA
<213> ORGANISM: Artificial Sequence
<220> FEATURE:
<223> OTHER INFORMATION: Oligonucleotide

<400> SEQUENCE: 27
gccttcctga ctgccgattg gtggaggcag                                    30

<210> SEQ ID NO 28
<211> LENGTH: 30
<212> TYPE: DNA
<213> ORGANISM: Artificial Sequence
<220> FEATURE:
<223> OTHER INFORMATION: Oligonucleotide

<400> SEQUENCE: 28
ctcttagagg tggagagatg ggagtaggct                                    30
```

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide

<400> SEQUENCE: 29
ctcttagagg tggagataag ggagtaggct                                    30

<210> SEQ ID NO 30
<211> LENGTH: 30
<212> TYPE: DNA
<213> ORGANISM: Artificial Sequence
<220> FEATURE:
<223> OTHER INFORMATION: Oligonucleotide

<400> SEQUENCE: 30
aattccactg catggcctga ggatgactgt                                    30

<210> SEQ ID NO 31
<211> LENGTH: 30
<212> TYPE: DNA
<213> ORGANISM: Artificial Sequence
<220> FEATURE:
<223> OTHER INFORMATION: Oligonucleotide

<400> SEQUENCE: 31
gatcctgcag agtttggtgg aaggcagtgg                                    30

<210> SEQ ID NO 32
<211> LENGTH: 27
<212> TYPE: DNA
<213> ORGANISM: Artificial Sequence
<220> FEATURE:
<223> OTHER INFORMATION: Oligonucleotide

<400> SEQUENCE: 32
atcttgaaga gtttggtgga aagtggt                                       27

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide

<400> SEQUENCE: 33
gatcttgaag agtttggtgg aaggtggtgg                                    30

<210> SEQ ID NO 34
<211> LENGTH: 27
<212> TYPE: DNA
<213> ORGANISM: Artificial Sequence
<220> FEATURE:
<223> OTHER INFORMATION: Oligonucleotide

<400> SEQUENCE: 34
atcttgaaga gtttggtgga aggtggt                                       27

<210> SEQ ID NO 35
<211> LENGTH: 30
<212> TYPE: DNA
<213> ORGANISM: Artificial Sequence
<220> FEATURE:
<223> OTHER INFORMATION: Oligonucleotide

```
<400> SEQUENCE: 35
gatcttgcag agcttggtgg aatgttgtgg                                      30

<210> SEQ ID NO 36
<211> LENGTH: 30
<212> TYPE: DNA
<213> ORGANISM: Artificial Sequence
<220> FEATURE:
<223> OTHER INFORMATION: Oligonucleotide

<400> SEQUENCE: 36
cagcaggaag atacagaccc ctgactctgg                                      30

<210> SEQ ID NO 37
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: r is a or g

<400> SEQUENCE: 37
agcaggaarg tacagggccc tgactct                                         27

<210> SEQ ID NO 38
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (11)..(11)
<223> OTHER INFORMATION: r is a or g
<220> FEATURE:
<221> NAME/KEY: misc_feature
<222> LOCATION: (14)..(14)
<223> OTHER INFORMATION: y is t or c

<400> SEQUENCE: 38
cagcaggaaa rtayaggccc ctcactctgg                                      30

<210> SEQ ID NO 39
<211> LENGTH: 30
<212> TYPE: DNA
<213> ORGANISM: Artificial Sequence
<220> FEATURE:
<223> OTHER INFORMATION: Oligonucleotide

<400> SEQUENCE: 39
cagggtttac tgttcctgaa ctggagccac                                      30

<210> SEQ ID NO 40
<211> LENGTH: 30
<212> TYPE: DNA
<213> ORGANISM: Artificial Sequence
<220> FEATURE:
<223> OTHER INFORMATION: Oligonucleotide

<400> SEQUENCE: 40
cagggctcac tgttcctgaa ctggagccac                                      30

<210> SEQ ID NO 41
<211> LENGTH: 30
<212> TYPE: DNA
```

<213> ORGANISM: Artificial Sequence
<220> FEATURE:
<223> OTHER INFORMATION: Oligonucleotide
<220> FEATURE:
<221> NAME/KEY: misc_feature
<222> LOCATION: (17)..(17)
<223> OTHER INFORMATION: k is g or t

<400> SEQUENCE: 41
cagggtttac tgttcckgaa ctggagccac                                30

<210> SEQ ID NO 42
<211> LENGTH: 30
<212> TYPE: DNA
<213> ORGANISM: Artificial Sequence
<220> FEATURE:
<223> OTHER INFORMATION: Oligonucleotide

<400> SEQUENCE: 42
ttgacgagat gtgagaggca atattcggag                                30

<210> SEQ ID NO 43
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (13)..(13)
<223> OTHER INFORMATION: y is t or c
<220> FEATURE:
<221> NAME/KEY: misc_feature
<222> LOCATION: (14)..(14)
<223> OTHER INFORMATION: m is c or a

<400> SEQUENCE: 43
ttgacgatat ggymgagaca gtattctgag                                30

<210> SEQ ID NO 44
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (14)..(14)
<223> OTHER INFORMATION: w is a or t

<400> SEQUENCE: 44
ttgacgatat gggwgaggca gtagtcggaa                                30

<210> SEQ ID NO 45
<211> LENGTH: 20
<212> TYPE: DNA
<213> ORGANISM: Artificial Sequence
<220> FEATURE:
<223> OTHER INFORMATION: PCR Primer

<400> SEQUENCE: 45
gagtctagac tctgcggtat                                           20

<210> SEQ ID NO 46
<211> LENGTH: 20
<212> TYPE: DNA
<213> ORGANISM: Artificial Sequence
<220> FEATURE:
<223> OTHER INFORMATION: PCR Primer

```
<400> SEQUENCE: 46
taacacgagc aggggtccta                                         20

<210> SEQ ID NO 47
<211> LENGTH: 17
<212> TYPE: DNA
<213> ORGANISM: Artificial Sequence
<220> FEATURE:
<223> OTHER INFORMATION: PCR Primer

<400> SEQUENCE: 47
gttttcccag tcacgac                                            17

<210> SEQ ID NO 48
<211> LENGTH: 22
<212> TYPE: DNA
<213> ORGANISM: Artificial Sequence
<220> FEATURE:
<223> OTHER INFORMATION: PCR Primer

<400> SEQUENCE: 48
tcacacagga aacagctatg ac                                      22

<210> SEQ ID NO 49
<211> LENGTH: 1203
<212> TYPE: DNA
<213> ORGANISM: Hepatitis B virus

<400> SEQUENCE: 49
atgggaggtt ggtcatcaaa acctcgcaaa ggcatgggga cgaatctttc tgttcccaat     60
cctctgggat tctttcccga tcatcagttg gaccctgcat tcggagccaa ctcaaacaat    120
ccagattggg acttcaaccc cgtcaaggac gactggccag cagccaacca agtaggagtg    180
ggagcattcg ggccaaggct caccccctcca cacggcggta ttttgggtg gagccctcag    240 gctcagggca tattgaccac agtgtcaaca attcctcctc ctgcctccac caatcggcag    300
tcaggaaggc agcctactcc catctctcca cctctaagag acagtcatcc tcaggccatg    360
cagtggaatt ccactgcctt ccaccaaact ctgcaggatc ccagagtcag gggtctgtat    420
cttcctgctg gtggctccag ttcaggaaca gtaaaccctg ctccgaatat gcctctcac     480 atctcgtcaa tctccgcgag gactggggac cctgtgacga catgagaga catcacatca    540 ggattcctag gaccctgct cgtgttacag gcggggtttt cttgttgac aagaatcctc     600 acaataccgc agagtctaga ctcgtggtgg acttctctca atttttctagg gggatctccc    660 gtgtgtcttg gccaaaattc gcagtcccca acctccaatc actcaccaac ctcctgtcct    720
ccaatttgtc ctggttatcg ctggatgtgt ctgcggcgtt ttatcatatt cctcttcatc    780
ctgctgctat gcctcatctt cttattggtt cttctggatt atcaaggtat gttgcccgtt    840
tgtcctctaa ttccaggatc aacaacaacc agtacgggac catgcaaaac ctgcacgact    900
cctgctcaag gcaactctat gtttccctca tgttgctgta caaaacctac ggatggaaat    960
tgcacctgta ttcccatccc atcgtcctgg gctttcgcaa ataccctatg ggagtgggcc    1020
tcagtccgtt tctcttggct cagtttacta gtgccatttg ttcagtggtt cgtagggctt    1080
tcccccactg tttggctttc agctatatgg atgatgtggt attggggggcc aagtctgtac    1140 agcatcgtga gtcccttttat accgctgtta ccaatttttct tttgtctctg gtatacatt     1200 taa                                                                    1203
```